United States Patent [19]

Lasley

[11] Patent Number: 4,474,571
[45] Date of Patent: Oct. 2, 1984

[54] PORTABLE TOPICAL HYPERBARIC CHAMBER ASSEMBLY

[76] Inventor: Robert A. Lasley, 508 Sentinel Rd., Moorestown, N.J. 08057

[21] Appl. No.: 428,239

[22] Filed: Sep. 29, 1982

[51] Int. Cl.³ ............................................. A61M 35/00
[52] U.S. Cl. .................................. 604/23; 128/202.12; 128/205.26
[58] Field of Search ................. 128/1 R, 30, 643, 644, 128/677, 205.26, 202.12, 205.22, 802, 206.24, 648, 246, 67, 132 R, 399, 400, 402; 604/23, 24, 289, 313, 305, 25, 73

[56] References Cited

U.S. PATENT DOCUMENTS 4,328,799 5/1982 LoPiano .......................... 128/205.26

FOREIGN PATENT DOCUMENTS 641061 8/1950 United Kingdom .................. 604/23

Primary Examiner—Lee S. Cohen
Assistant Examiner—Steven Falk
Attorney, Agent, or Firm—Witherspoon & Hargest

[57] ABSTRACT

A portable topical hyperbaric chamber assembly for covering a surface portion of the patient's body for treatment with pressurized oxygen. The assembly comprises a circular base with a plurality of support and positioning rods extending downwardly from the peripheral portion of the base. A resilient circular gasket, open at its top and bottom, snugly fitted into the circular area defined by the rods depending from the base so that its top snugly engages the bottom surface of the base for sealing purposes and the bottom engages the skin of the patient for sealing. The base is equipped with connections for attaching various hoses from the pressurized oxygen control device.

7 Claims, 4 Drawing Figures

4,474,571

PORTABLE TOPICAL HYPERBARIC CHAMBER ASSEMBLY

BACKGROUND AND SUMMARY OF THE INVENTION

This invention relates to a portable hyperbaric chamber assembly and more particularly a topical hyperbaric chamber assembly wherein the chamber assembly is provided with an opening surrounded by a sealable edge so that said opening may be positioned over the wound to be treated and the sealable edge will engage the patient's skin.

Most of the hyperbaric chambers presently in use are of the type wherein a portion of the patient's body is placed within the pressurized chamber. Such chambers make treatment of certain portions of the patient's body very difficult since large units are required when the area to be treated is on the upper torso of a patient.

In view of the foregoing it is an object of this invention to provide a hyperbaric chamber assembly which is adapted to treat designated areas over a patient's body.

It is another object of this invention to provide a topical hyperbaric chamber assembly having an opening surrounded by a sealable edge of such configuration that it will engage the patient's skin surrounding the treatment area and responds to the pressure within the chamber to assure an airtight seal and yet not cause the patient any discomfort in the seal area.

It is yet another object of this invention to provide a topical hyperbaric chamber assembly wherein the assembly includes a gasket forming a chamber having at least one opening surrounded by a sealable lip adapted to engage the patient's skin.

It is a still further object of this invention to provide a gasket with openings on the top and bottom of different sizes and is reversible.

The foregoing and additional objects and advantages will become more apparent when taken in conjuction with the following detailed description and drawings, showing by use of example a preferred embodiment of this invention.

IN THE DRAWINGS

FIG. 1 is a perspective view of the hyperbaric chamber of this invention applied to a patient, FIG. 2 is an exploded perspective view of the components of the hyperbaric chamber of this invention, FIG. 3 is a vertical cross sectional view illustrating the manner in which the gasket is securred to the hyperbaric chamber base and FIG. 4 is a plan view of the gasket illustrated in FIG. 3.

DETAILED DESCRIPTION

Figure 2:
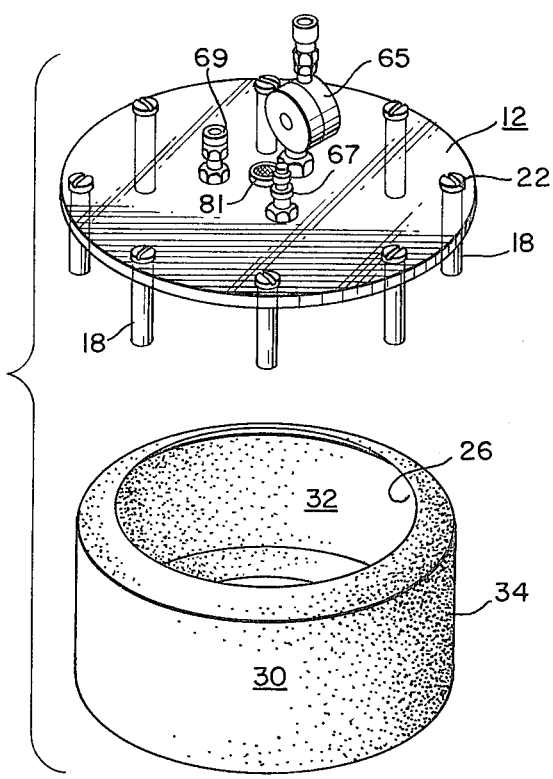
Figure 3:
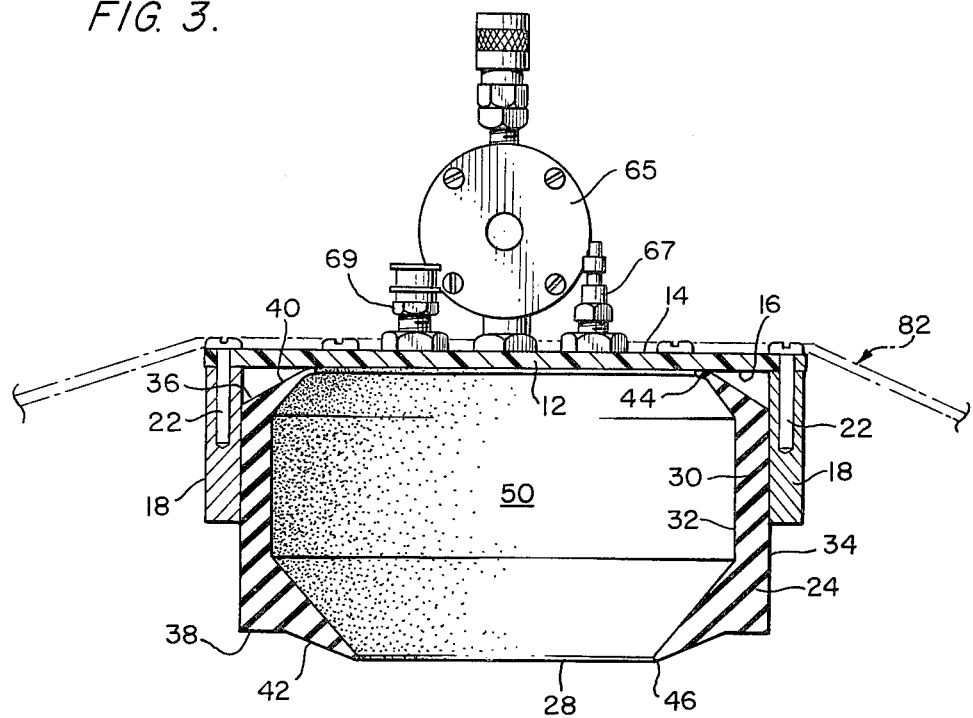
Figure 4:
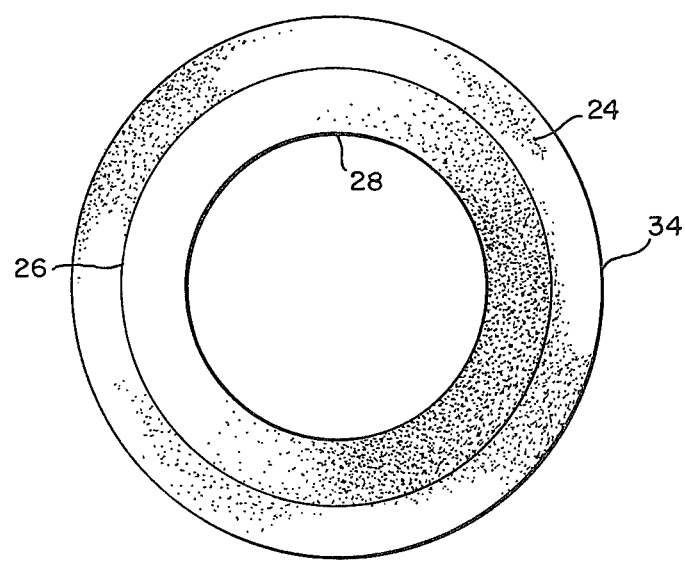

As best illustrated in FIGS. 2, 3 and 4, the hyperbaric chamber assembly 10 comprises a flat circular base 12 of clear plastic material having a top surface 14 and a bottom surface 16. A plurality of support and positioning rods 18 extend downwardly from the periphery of the base bottom surface 16. Each rod 18 is secured to the base 12 by means of a screw 22.

A circular resilient gasket 24 fits into the circular area defined by the downwardly extending rods 18. The gasket 24 has an open circular top 26 and a bottom circular opening 28 of smaller diameter than the top opening.

More specifically, the circular resilient gasket 24 has a vertical cylindrical body 30 with an outer wall 32 and an inner wall 34. The body 30 has a top portion 36 and a bottom portion 38 with a top flange 40 extending radially and inwardly from the top portion 36 and a bottom flange 42 extending radially and inwardly from the bottom portion 38. The top flange 40 terminates in a feather lip portion 44 whose extremity forms the body top opening 26. The bottom flange 42 terminates in a feather lip 46 whose entremity forms the bottom body opening 28.

When the gasket 24 is assembled with the base 12 as illustrated in FIG. 3, the vertical outer wall 32 of the body 30 engages supports and positioning rods 18 to retain the gasket 24 in position. It should be noted that the gasket 24 is forced into the circular area defined by the rods 18 so that the feather lip 44 of top flange 40 is snugly forced against the bottom surface 16 of the base 12 to form an air tight seal therebetween when gas pressure is applied to the chamber 50 formed by the gasket 24 and the bottom surface 16 of the base 12. The closing of the chamber 50 is completed when the chamber assembly 10 is placed on the patient with the bottom feather lip 46 sealingly engaging the skin surface of the patient.

Figure 1:
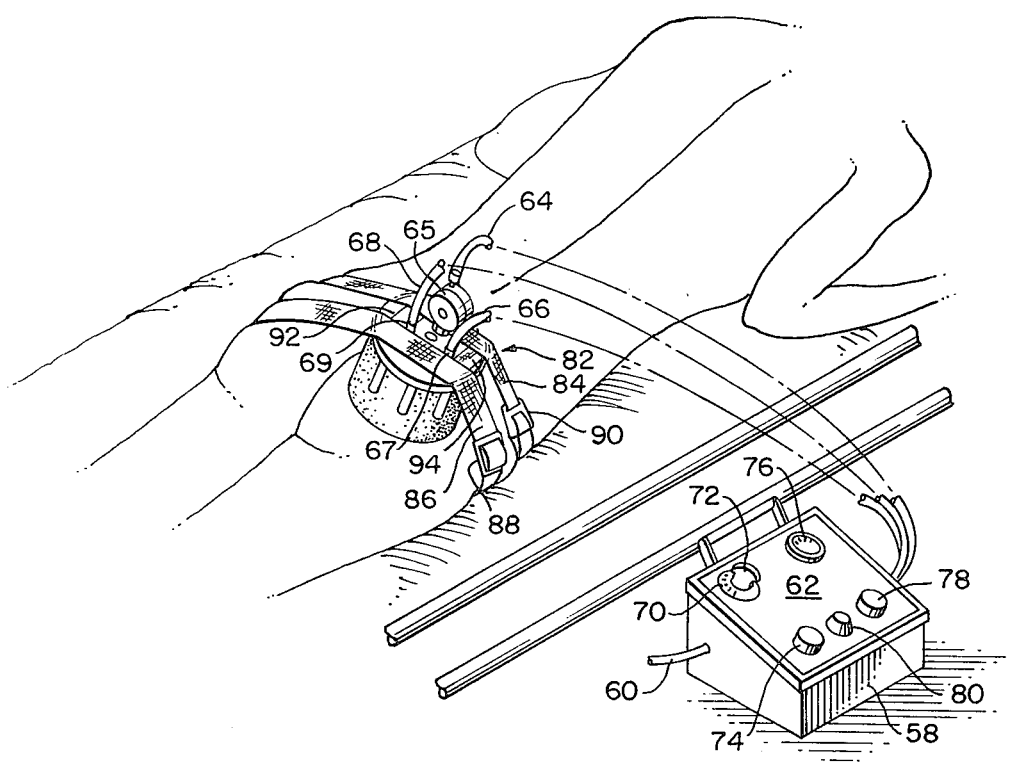

The top surface 14 of the base 12 is provided with connections for receiving hoses from the pressurized gas control units. As illustrated in FIGS. 1, 2 and 3, the means 60 for controlling flow of pressurized oxygen or other suitable gas to the chamber assembly 10 and exhausting same therefrom may be of the type described in Lasley U.S. Pat. No. 4,296,743 wherein a control device is disclosed which is completely fluid operated. For the purpose of making this disclosure clear a small portion of the description of such control device is set forth hereinafter.

Pressurized oxygen is fed through tube 60 to control box 62 and comes out of said control box through hose 64 which introduces pressurized oxygen into chamber exhaust valve 65 to hold same in the closed condition as long as pressure is maintained therein. The main feed of pressurized oxygen comes out through hose 66 into the chamber 50 by way of hose connection 67. Hose 68 is connected to hose connection 69 and feeds pressurized gas from the chamber 50 to a pressure gauge.

More specifically, the control box 62 includes a timer dial 70 with an on/off timer setting knob 72 and a cycle timing control screw 74. Chamber pressure gauge 76 measures the pressure within chamber 50 through hose 68. Pressure adjusting knob 78 controls the operating pressure within the chamber 50. An air lite 80 is provided to determined when the device is operating. Air lites of this type are sold by C.A. Norgen Company of Littleton, Colorado and are known as Rotowink Indicators. The unit is also provided with a safety relief valve 81 located in the base 12.

In use, the resilient gasket 24 is inserted into the area formed by the rods 18 so that the outer surface 34 of the body 30 frictionally engages the rods 18 and the upper flange feather lip 44 snugly engages the bottom surface 16 of the base 12. Next the securing strap assembly 82 is assembled onto the chamber unit 10. Specifically, the strap assembly 82 comprises a pair of generally coextensive straps 84 and 86, each of which is provided a safety buckle 88 and 90 respectively. The two straps 84 and 86 are held together by connecting spaced cross straps 92 and 94 which together with portions of straps 84 and 86 form an opening which fits over and around the hose connections on the base 12.

As shown in FIG. 1, the opening in the strap assembly 82 is place over and around the hose connections on the base 12 after which the gasket 24 is placed over the wound to be treated with the feather lip 44 of flange 42 smoothly engaing the patient's skin. Next the straps 84 and 86 are passed around the patient and held snugly in such position by the safety buckles 88 and 90. Thus the hyperbaric chamber assembly 10 is positioned on the patient. Next the connections are made from the control box 62 to the connections on the base 12. The apparatus is now ready for action.

The application of pressure in the chamber 50 will cause feather lips 44 and 46 to form air tight seals with respect to the bottom face 16 of the base 12 and the skin of the patient, respectively. The great degree of flexibility of the gasket material and the feather lips requires such a small amount of pressure that the patient will experience no unpleasant sensation from such. The fact that the gasket 24 is reversible depending upon the diameter of opening required is a distinct advantage. Further, the ease of assembly and disassembly greatly adds to the units overall usefulness, i.e. no tools are needed to assemble the unit or to reverse the gaskets.

What is claimed is:

1. A portable topical hyperbaric chamber for enclosing a surface portion of the patient's body for treatment with oxygen or other gas at pressures slightly above atmospheric said portable chamber comprising:

a flat circular base having a top face and a bottom face, a plurality of support and positioning rods secured to and extending downwardly from the peripheral edge portion of the bottom face of the circular base to define a circular area, a circular resilient gasket having a top and a bottom, open at its bottom, fitted into the circular area defined by the support and positioning rods, the top of said gasket being adjacent the flat circular base, said gasket having a cylindrical body with a vertical outside wall sized to fit within the area defined by the said rods and engaged thereby to retain the gasket in position, said cylindrical body having a top portion and a bottom portion, a flange extending radially and inwardly from the bottom portion of the body, said flange terminating in a feather lip to form the bottom of the gasket being adapted to sealingly contact the patient's skin surrounding the wound to be treated and the base being provided with connections to receive a controlled supply of pressurized oxygen or other suitable gas, said connections communicating with the interior of the gasket.

2. The invention as set forth in claim 1 and wherein the circular resilient gasket is provided with an opening at its top and at its bottom.

3. The invention as set forth in claim 2 and wherein the openings in the top and bottom of the gasket are of different sizes and the gasket is reversible whereby the chamber may conveniently be used in treating wounds of different sizes.

4. The invention as set forth in claim 1 and wherein the flat circular base is provided with a safety exhaust valve.

5. The invention as set forth in claim 1 and wherein the flat circular base is transparent to thereby aid in properly positioning the chamber over the wound.

6. The invention as set forth in claim 1 and wherein flexible strap means are provided to secure the chamber to the patient.

7. The invention as set forth in claim 2 and wherein a flange extends radially inward from the top portion of the body, said flange terminating in a feather lip to form said top opening, the lip of the flange extending from the top flange sealingly engaging the bottom face of the base.

* * * * *